(12) United States Patent
Prendergast et al.

(10) Patent No.: US 8,389,568 B2
(45) Date of Patent: Mar. 5, 2013

(54) IDO INHIBITORS AND METHODS OF USE THEREOF

(75) Inventors: George C. Prendergast, Penn Valley, PA (US); William P. Malachowski, Collegeville, PA (US); Alexander J. Muller, Media, PA (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 477 days.

(21) Appl. No.: 12/528,466

(22) PCT Filed: Mar. 14, 2008

(86) PCT No.: PCT/US2008/057032
§ 371 (c)(1),
(2), (4) Date: Dec. 3, 2009

(87) PCT Pub. No.: WO2008/115804
PCT Pub. Date: Sep. 25, 2008

(65) Prior Publication Data
US 2010/0076066 A1    Mar. 25, 2010

Related U.S. Application Data

(60) Provisional application No. 60/918,516, filed on Mar. 16, 2007.

(51) Int. Cl.
*A61K 31/205* (2006.01)
*C07D 311/82* (2006.01)
*C07D 311/92* (2006.01)
(52) U.S. Cl. ......... 514/454; 514/455; 549/388; 549/389
(58) Field of Classification Search .................. 549/388, 549/389; 514/454, 455
See application file for complete search history.

(56) References Cited

U.S. PATENT DOCUMENTS

| 5,043,166 | A | 8/1991 | Barenholz et al. |
| 5,606,037 | A | 2/1997 | Attardo et al. |
| 5,736,523 | A | 4/1998 | Attardo et al. |
| 2004/0234623 | A1 | 11/2004 | Munn et al. |
| 2004/0266857 | A1 | 12/2004 | Jiang et al. |
| 2006/0258719 | A1 | 11/2006 | Combs et al. |

FOREIGN PATENT DOCUMENTS

| WO | 97/08162 | 3/1997 |
| WO | 2002/076939 | 10/2002 |
| WO | 03/090710 | 11/2003 |
| WO | 2004/045557 | 6/2004 |
| WO | 2006/005185 | 1/2006 |

OTHER PUBLICATIONS

Gupta, R., et al. "The total synthesis of (−)-cryptosporin." Journal of the American Chemical Society.1989;111 (19):7668-70.
Krohn, K., et al. "Synthesis of 6-deoxycryptosporin and related compounds." Chemische Berichte. 1978;111 (4):1284-93.
Lee, Y.K., et al. "A concise route for the synthesis of pyranonaphthoquinone derivatives." Synthesis. 2005;18:3026-3034.
Krohn, K., et al. "Synthesis of 6-deoxycrytosporin." Tetrahedron Letters. 1977;14:1265-8.
Sacau, E.P., et al. "Inhibitory effects of lapachol derivatives on epstein-barr virus activation." Bioorg Med Chem. Feb. 20, 2003;11(4):483-8.
Itoigawa, M., et al. "Cancer chemopreventive activity of naphthoquinones and their analogs from Avicennia plants." Cancer Lett. Dec. 28, 2001;174(2):135-9.
Tapia, R.A., et al. "Synthesis of 2,2-Dimethyl-3, 4-Epoxy-2 H-Naphtho[2,3-b]Pyran-5, 10-Dione." Synthetic Communications: An International Journal for Rapid Communication of Synthetic Organic Chemistry. 2001;31(4):601-606.
Fujiwara, A., et al. "Antitumor-promoting naphthoquinones from Catalpa ovata." J Nat Prod. May 1998;61(5):629-32.
Pinto, A.V., et al. "Antiviral activity of naphthoquinones. I. Lapachol derivatives against enteroviruses." Rev Latinoam Microbiol. Jan.-Mar. 1987:29(1):15-20.

*Primary Examiner* — Shengjun Wang
(74) *Attorney, Agent, or Firm* — Dann Dorfman Herrell & Skillman; Robert C. Netter, Jr.

(57) ABSTRACT

Novel indoleamine 2,3-dioxygenase (IDO) inhibitors, compositions comprising the same, and methods of use thereof are disclosed.

15 Claims, 5 Drawing Sheets

IDO INHIBITORS AND METHODS OF USE THEREOF

This application is a §371 application of PCT/US2008/057032, filed Mar. 14, 2008, which claims priority under 35 U.S.C. §119(e) to U.S. Provisional Patent Application No. 60/918,516, filed on Mar. 16, 2007. The foregoing applications are incorporated by reference herein.

Pursuant to 35 U.S.C. Section 202(c), it is acknowledged that the United States Government has certain rights in the invention described herein, which was made in part with funds from the National Institutes of Health Grant No. R01-CA109542.

FIELD OF THE INVENTION

This invention relates to the field of oncology. Specifically, the invention provides novel chemotherapeutic agents and methods of using such agents for the treatment of cancer.

BACKGROUND OF THE INVENTION

Tumors characteristically express atypical, potentially immunoreactive antigens that are collectively referred to as tumor antigens. Accumulating evidence suggests that the failure of the immune system to mount an effective response against progressively growing tumors is not attributable to a lack of recognizable tumor antigens. Immunosuppression by tumors is poorly understood and mechanisms by which tumors may escape immune surveillance have been poorly explored. Recently, it has been shown that cytotoxic T cells become tolerized by a reduction in local concentrations of tryptophan that are elicited by indoleamine 2,3-dioxygenase (IDO; EC 1.13.11.42) activity. Furthermore, IDO has been implicated in tumor immunosuppression (Muller et al. (2005) Nat. Med., 11:312-9; Munn et al. (2004) Trends Mol. Med., 10:15-18; Uyttenhove et al. (2003) Nat. Med., 9:1269-74; Friberg et al. (2002) Intl. J. Cancer, 101:151-155).

Dietary catabolism of tryptophan is mediated by the structurally unrelated liver enzyme tryptophan dioxygenase (TDO2; 1.13.11.11). IDO is an extrahepatic oxidoreductase that catalyzes the initial and rate-limiting step in the degradation of tryptophan along the kynurenine pathway that leads to the biosynthesis of nicotinamide adenine dinucleotide ($NAD^+$) (Sono et al. (1996) Chem. Rev., 96:2841-87; Botting et al. (1995) Chem. Soc. Rev., 24:401-12; Sono et al. (1980) Biochem. Rev., 50:173-81). IDO is a monomeric 45 kDa heme-containing oxidase that is active with the heme iron in the ferrous ($Fe^{+2}$) form. The ferric ($Fe^{+3}$) form of IDO is inactive and substrate inhibition is believed to result from tryptophan (Trp) binding to ferric IDO (Sono et al. (1980) J. Biol. Chem., 255:1339-45; Kobayashi et al. (1989) J. Biol. Chem., 264:15280-3). The primary catalytic cycle of IDO does not involve redox changes, nevertheless IDO is prone to autooxidation and therefore a reductant is necessary to reactivate the enzyme. In vivo, IDO purportedly relies on a flavin or tetrahydrobiopterin co-factor. In vitro, methylene blue and ascorbic acid are believed to substitute for the natural flavin or tetrahydrobiopterin co-factor.

Inhibition of IDO has previously been targeted for other therapies, most notably neurological disorders (Botting et al. (1995) Chem. Soc. Rev., 24:401-12). Several metabolites of the kynurenine pathway are neurotoxic or are implicated in neurodegeneration, e.g. quinolinic acid, and therefore attention has focused on IDO. A recent review summarizes the range of compounds that have been tested as IDO inhibitors (Muller et al. (2005) Expert. Opin. Ther. Targets., 9:831-49).

SUMMARY OF THE INVENTION

In accordance with one aspect of the invention, novel inhibitors of indoleamine 2,3-dioxygenase (IDO) activity are provided.

In one embodiment, the novel IDO inhibitor has the formula:

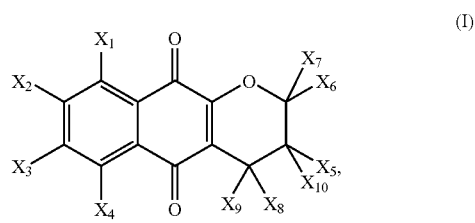

(I)

wherein $X_9$ and $X_{10}$ are H or OH and wherein $X_1$, $X_2$, $X_3$, $X_4$, $X_5$, $X_6$, $X_7$, and $X_8$ are independently selected from the group consisting of halide, H, OH, R, OR, NHR, and SR, and wherein R is an optionally substituted; saturated or unsaturated; linear, branched or cyclic alkyl group or an optionally substituted aryl group. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

In another embodiment, the novel IDO inhibitor has the formula:

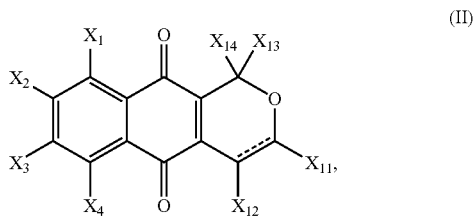

(II)

wherein $X_1$, $X_2$, $X_3$, $X_4$, $X_{11}$, $X_{12}$, $X_{13}$, and $X_{14}$ are independently selected from the group consisting of halide, H, OH, R, OR, NHR, and SR, and wherein R is an optionally substituted; saturated or unsaturated; linear, branched or cyclic alkyl group or an optionally substituted aryl group. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

In still another embodiment, the novel IDO inhibitor has the formula:

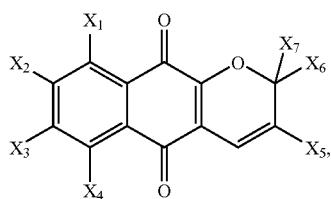

(III)

wherein $X_1$, $X_2$, $X_3$, $X_4$, $X_5$, $X_6$, and $X_7$, are independently selected from the group consisting of halide, H, OH, R, OR, NHR, and SR, and wherein R is an optionally substituted; saturated or unsaturated; linear, branched or cyclic alkyl group or an optionally substituted aryl group. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

In yet another embodiment of the invention, the novel IDO inhibitor is selected from the group consisting of compounds 8-22 and 26-29. In still another embodiment, the novel IDO inhibitor is the hydroquinone form of the above IDO inhibitors, e.g., the compounds of formula (I), (II), and (III).

According to another aspect of the present invention, methods are provided for treating cancer in a patient. The methods comprise administering an effective amount of a pharmaceutical composition comprising at least one IDO inhibitor in a pharmaceutically acceptable carrier medium, wherein at least one of the IDO inhibitors is selected from the group consisting of compounds of formula (I), (II), and (III). In another embodiment, the method further comprises administering to the patient, concurrently or sequentially, an effective amount of at least one signal transduction inhibitor (STI) which may be administered in a pharmaceutically acceptable carrier. In still another embodiment of the invention, the method further comprises administering to the patient, concurrently or sequentially, an effective amount of at least one chemotherapeutic agent which may be in a pharmaceutically acceptable carrier.

In yet another embodiment of the present invention, methods are provided for treating a chronic viral infection in a patient in need thereof by administering to the patient, concurrently or sequentially, an effective amount of at least one indoleamine 2,3-dioxygenase (IDO) inhibitor and at least one chemotherapeutic agent.

In accordance with another aspect of the instant invention, pharmaceutical compositions comprising the above-described compounds are provided for administration in carrying out the above methods.

DETAILED DESCRIPTION OF THE INVENTION

Figure 1:
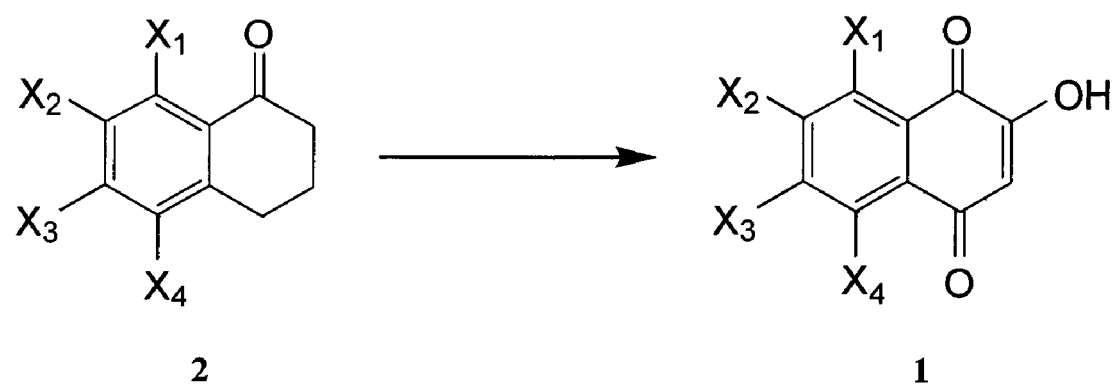
FIG. 1 provides a scheme for the synthesis of 2-hydroxy-1,4-napthoquinones.

In accordance with the instant invention, a series of napthoquinone derivatives were screened to determine their ability to inhibit IDO. IDO inhibitors of the instant invention may have the formula:

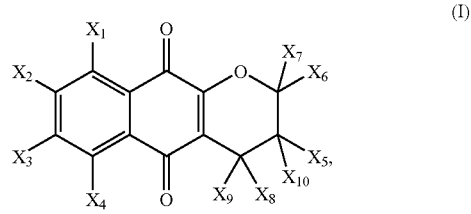

(I)

wherein $X_9$ and $X_{10}$ are H or OH and wherein $X_1$, $X_2$, $X_3$, $X_4$, $X_5$, $X_6$, $X_7$, and $X_8$ are independently selected from the group consisting of halide, H, OH, R, OR, NHR, and SR, and wherein R is an alkyl group or aryl group. The aryl group may be substituted. The alkyl group may be 1) substituted, 2) saturated or unsaturated, and/or 3) linear, branched or cyclic. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

The novel IDO inhibitors of the instant invention may also have the formula:

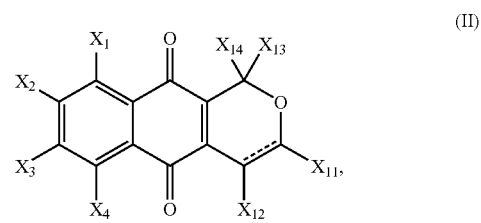

(II)

wherein $X_1$, $X_2$, $X_3$, $X_4$, $X_{11}$, $X_{12}$, $X_{13}$, and $X_{14}$ are independently selected from the group consisting of halide, H, OH, R, OR, NHR, and SR, and wherein R is an alkyl group or aryl group. The aryl group may be substituted. The alkyl group may be 1) substituted, 2) saturated or unsaturated, and/or 3) linear, branched or cyclic. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups. The dashed line indicates that the bond is either a single or double bond.

The novel IDO inhibitors of the instant invention may also have the formula:

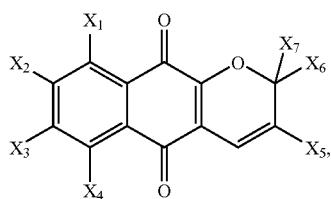

(III)

wherein $X_1$, $X_2$, $X_3$, $X_4$, $X_5$, $X_6$, and $X_7$ are independently selected from the group consisting of halide, H, OH, R, OR, NHR, and SR, and wherein R is an alkyl group or aryl group. The aryl group may be substituted. The alkyl group may be 1) substituted, 2) saturated or unsaturated, and/or 3) linear, branched or cyclic. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

The novel IDO inhibitors of the instant invention may also be the hydroquinone form of the above IDO inhibitors.

I. DEFINITIONS

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

IDO inhibitors may include, without limitation, i) previously established (known) IDO inhibitors, including, but not limited to: 1-methyl-DL-tryptophan (1MT; Sigma-Aldrich; St. Louis, Mo.), β-(3-benzofuranyl)-DL-alanine (Sigma-Aldrich), beta-(3-benzo(b)thienyl)-DL-alanine (Sigma-Aldrich), 6-nitro-L-tryptophan (Sigma-Aldrich), indole 3-carbinol (LKT Laboratories; St. Paul, Minn.), 3,3'-diindolylmethane (LKT Laboratories), epigallocatechin gallate (LKT Laboratories), 5-Br-4-Cl-indoxyl 1,3-diacetate (Sigma-Aldrich), 9-vinylcarbazole (Sigma-Aldrich), acemetacin (Sigma-Aldrich), 5-bromo-DL-tryptophan (Sigma-Aldrich), 5-bromoindoxyl diacetate (Sigma-Aldrich), and the IDO inhibitors provided in PCT/US04/05155, PCT/US04/05154, PCT/US06/42137, and U.S. patent application Ser. No. 11/589,024; and ii) the novel IDO inhibitors of the instant invention. In a preferred embodiment of the invention, the IDO inhibitors include the novel IDO inhibitors of the present invention.

A "signal transduction inhibitor" is an agent that selectively inhibits one or more vital steps in signaling pathways, in the normal function of cancer cells, thereby leading to apoptosis. Signal transduction inhibitors (STIs) include, but are not limited to, (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), Clin Cancer Res. 1:1311-1318], and Abgenix: ABX-EGF); (iii) her-2/neu receptor inhibitors such as, for example, Herceptin™ (trastuzumab), and farnesyl transferase inhibitors (FTI) such as, for example, L-744,832 (Kohl et al. (1995), Nat Med. 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248). In a particular embodiment, the STI is selected from the group consisting of STI 571, SSI-774, C225, ABX-EGF, trastuzumab, L-744, 832, rapamycin, LY294002, flavopiridal, and UNC-01. In yet another embodiment, the STI is L-744,832.

The term "chemotherapeutic agent" refers generally to any compound that exhibits anticancer activity. Chemotherapeutic agents include, but are not limited to: alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). Preferably, the chemotheraputic agent is selected from the group consisting of: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

A "therapeutically effective amount" of a compound or a pharmaceutical composition refers to an amount effective to prevent, inhibit, or treat the symptoms of a particular disorder or disease. For example, "therapeutically effective amount" may refer to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxiliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Concurrently" means (1) simultaneously in time, or (2) at different times during the course of a common treatment schedule.

"Sequentially" refers to the administration of one component of the method followed by administration of the other component. After administration of one component, the next component can be administered substantially immediately after the first component, or the next component can be administered after an effective time period after the first component; the effective time period is the amount of time given for realization of maximum benefit from the administration of the first component.

The term "alkyl," as employed herein, includes both straight and branched chain hydrocarbons containing 1 to 10 carbons, preferably 1 to 8 carbons, more preferably 1 to 4 carbons, in the normal chain. The hydrocarbon chain of the alkyl groups may be interrupted with oxygen, nitrogen, or sulfur. Examples of suitable alkyl groups include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, the various branched chain isomers thereof, and the like. Each alkyl group may optionally be substituted with 1 to 4 substituents which include, for example, halo, —OH, and alkyl.

The term "cyclic alkyl" or "cycloalkyl," as employed herein, includes cyclic hydrocarbon groups containing 1 to 3 rings which may be fused or unfused. Cycloalkyl groups may contain a total of 3 to 20 carbons forming the ring(s), preferably 6 to 10 carbons forming the ring(s). Optionally, one of the rings may be an aromatic ring as described below for aryl. Cycloalkyl groups may contain one or more double bonds. The cycloalkyl groups may also optionally contain substituted rings that includes at least one, and preferably from 1 to about 4 sulfur, oxygen, or nitrogen heteroatom ring members. Each cycloalkyl group may be optionally substituted with 1 to about 4 substituents such as alkyl (an optionally substituted straight, branched or cyclic hydrocarbon group, optionally saturated, having from about 1-10 carbons, particularly about 1-4 carbons), halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or $NHRC(=O)$—, wherein R is an alkyl), urea (—$NHCONH_2$), alkylurea, aryl, ether, ester, thioester, nitrile, nitro, amide, carbonyl, carboxylate and thiol. Exemplary cycloalkyls include, without limitation, indanyl and adamantyl.

"Alkenyl" refers to an unsubstituted or substituted hydrocarbon moiety comprising one or more carbon to carbon double bonds (i.e., the alkenyl group is unsaturated) and containing from 1 to about 12 carbon atoms or from 1 to about 5 carbon atoms, which may be a straight, branched, or cyclic hydrocarbon group. When substituted, alkenyl groups may be substituted at any available point of attachment. Exemplary substituents may include, but are not limited to, alkyl, halo, haloalkyl, alkoxyl, alkylthio, hydroxyl, methoxy, carboxyl, oxo, epoxy, alkyloxycarbonyl, alkylcarbonyloxy, amino, carbamoyl, urea, alkylurea, and thiol. Preferably, the alkenyl group comprises alternating double and single bonds such that bonds are conjugated. Exemplary alkenyl groups include, without limitation, allyl and 1,3-butadienyl.

The term "aryl," as employed herein, refers to monocyclic and bicyclic aromatic groups containing 6 to 10 carbons in the ring portion. Examples of aryl groups include, without limitation, phenyl, naphthyl, such as 1-naphthyl and 2-naphthyl, indolyl, and pyridyl, such as 3-pyridyl and 4-pyridyl. Aryl groups may be optionally substituted through available carbon atoms with 1 to about 4 groups. Exemplary substituents may include, but are not limited to, alkyl, halo, haloalkyl, alkoxyl, alkylthio, hydroxyl, methoxy, carboxyl, carboxylate, oxo, ether, ester, epoxy, alkyloxycarbonyl, alkylcarbonyloxy, amino, carbamoyl, urea, alkylurea, thioester, amide, nitro, carbonyl, and thiol. The aromatic groups may be heteroaryl. "Heteroaryl" refers to an optionally substituted aromatic ring system that includes at least one, and preferably from 1 to about 4 sulfur, oxygen, or nitrogen heteroatom ring members.

II. NOVEL COMPOUNDS EXHIBITING IDO INHIBITORY ACTIVITY

In accordance with the instant invention, novel compounds are provided which are capable of inhibiting IDO activity.

In one embodiment, the novel IDO inhibitor has the formula:

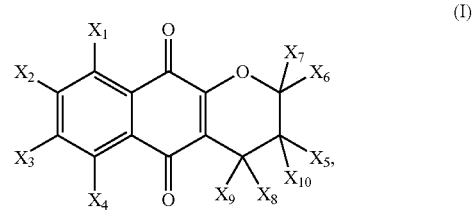

(I)

wherein $X_9$ and $X_{10}$ are H or OH and wherein $X_1$, $X_2$, $X_3$, $X_4$, $X_5$, $X_6$, $X_7$, and $X_8$ are independently selected from the group consisting of halide, H, OH, R, OR, NHR, and SR, and wherein R is an optionally substituted; saturated or unsaturated; linear, branched or cyclic alkyl group or an optionally substituted aryl group. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

In another embodiment, the novel IDO inhibitor has the formula:

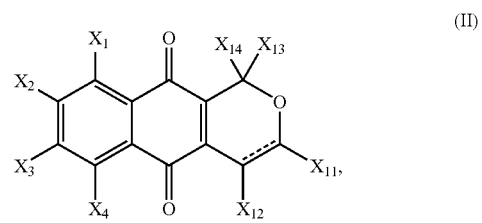

(II)

wherein $X_1$, $X_2$, $X_3$, $X_4$, $X_{11}$, $X_{12}$, $X_{13}$, and $X_{14}$ are independently selected from the group consisting of halide, H, OH, R, OR, NHR, and SR, and wherein R is an optionally substituted; saturated or unsaturated; linear, branched or cyclic alkyl group or an optionally substituted aryl group. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

In still another embodiment, the novel IDO inhibitor has the formula:

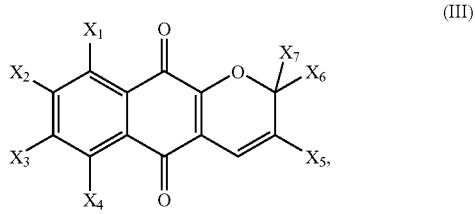

(III)

wherein $X_1$, $X_2$, $X_3$, $X_4$, $X_5$, $X_6$, and $X_7$, are independently selected from the group consisting of halide, H, OH, R, OR, NHR, and SR, and wherein R is an optionally substituted; saturated or unsaturated; linear, branched or cyclic alkyl group or an optionally substituted aryl group. The substitution of the R group may refer to the presence of substituents selected from the group consisting of aryl, ether, amino, hydroxyl, ester, thioether, thiol, nitrile, nitro, amide, carbonyl, carboxyl, carboxylate, and halide groups. Where R is an aryl group, or is substituted by an aryl group, the aryl group may be optionally substituted with ether, amino, hydroxyl, ester, thioether, amide, nitro, carbonyl, carboxyl, carboxylate and halide groups.

In yet another embodiment of the invention, the novel IDO inhibitor is selected from the group consisting of compounds 8-22 and 26-29. In yet another embodiment of the invention, the IDO inhibitor is the hydroquinone form of the above novel IDO inhibitors.

III. THERAPIES AND COMPOSITIONS FOR THE TREATMENT OF CANCER AND VIRAL INFECTIONS

The present invention provides pharmaceutical compositions comprising at least one of the IDO inhibitors of the instant invention in a pharmaceutically acceptable carrier. Such a pharmaceutical composition may be administered, in a therapeutically effective amount, to a patient in need thereof for the treatment of cancer. The pharmaceutical compositions may comprise at least one IDO inhibitor of the instant invention in addition to at least one established (known) IDO inhibitor. In a specific embodiment, at least one of the IDO inhibitors of the pharmaceutical composition is selected from the group consisting of compounds of formulas (I), (II), and (III).

Moreover, the present invention provides a method for the treatment of cancer by administering to a patient, in need thereof, a therapeutically effective amount of the compounds of the instant invention, preferably in the form of a pharmaceutical composition. In a particular embodiment, at least one the IDO inhibitors administered in the method of treating cancer is selected from the group consisting of compounds of formulas (I), (II), and (III).

The pharmaceutical composition may further comprise at least one signal transduction inhibitor (STI) (see, e.g., PCT/US04/05155 and PCT/US04/05154). Suitable STIs, as noted hereinabove, include, but are not limited to: (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), Clin Cancer Res. 1:1311-1318], and Abgenix: ABX-EGF); (iii) her-2/neu receptor inhibitors such as, for example, Herceptin™ (trastuzumab) and farnesyl transferase inhibitors (FTI) such as, for example, L-744,832 (Kohl et al. (1995), Nat Med. 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The pharmaceutical compositions of the invention may further comprise at least one chemotherapeutic agent. Suitable chemotherapeutic agents are described hereinabove. Preferred chemotherapeutic agents include, but are not limited to: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. In a particular embodiment, the chemotherapeutic agent is paclitaxel. As an alternative, the at least one chemotherapeutic agent and the at least on IDO inhibitor may be in separate pharmaceutical compositions. In a particular embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and at least one chemotherapeutic agent may be administered at the same time. Additionally, when more than one IDO inhibitor and/or chemotherapeutic agent and/or STI is used, the compounds may be administered in any order.

Cancers that may be treated using the present protocol include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may comprise at least one IDO inhibitor of the instant invention in addition to at least one established (known) IDO inhibitor. In a specific embodiment, at least one of the IDO inhibitors of the pharmaceutical composition is selected from the group consisting of compounds of formulas (I), (II), and (III).

Also provided is a method for treating a chronic viral infection in a patient by administering an effective amount of the above pharmaceutical composition. In a particular embodiment, at least one of the IDO inhibitors administered in the method of treating a viral infection is selected from the group consisting of compounds of formulas (I), (II), and (III).

Suitable antiviral agents include, without limitation: acyclovir; gangcyclovir; foscarnet; ribavirin; and antiretrovirals such as, for example, nucleoside analogue reverse transcriptase inhibitors (e.g., azidothymidine (AZT), ddI, ddC, 3TC, d4T), non-nucleoside reverse transcriptase inhibitors (e.g., efavirenz, nevirapine), nucleotide analogue reverse transcriptase inhibitors, and protease inhibitors.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

The compounds of this combination treatment may also be administered for localized infections. Specifically, at least one IDO inhibitor, optionally, at least one chemotherapeutic agent, and, optionally, at least one antiviral agent may be administered to treat skin infections such as shingles and warts. The compounds may be administered in any pharmaceutically acceptable topical carrier including, without limitation: gels, creams, lotions, ointments, powders, aerosols and other conventional forms for applying medication to the skin.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al. (2004) Circulation, 110:810-814).

IV. ADMINISTRATION OF PHARMACEUTICAL COMPOSITIONS AND COMPOUNDS

The pharmaceutical compositions of the present invention can be administered by any suitable route, for example, by injection, by oral, pulmonary, nasal or other modes of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321: 574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate immune activation or a tumor. Other controlled release systems are discussed in the review by Langer (Science (1990) 249:1527-1533).

The following examples are provided to illustrate various embodiments of the present invention. These examples are not intended to limit the invention in any way.

Example 1

Synthesis of Compounds of Formulas I and III

Figure 3:
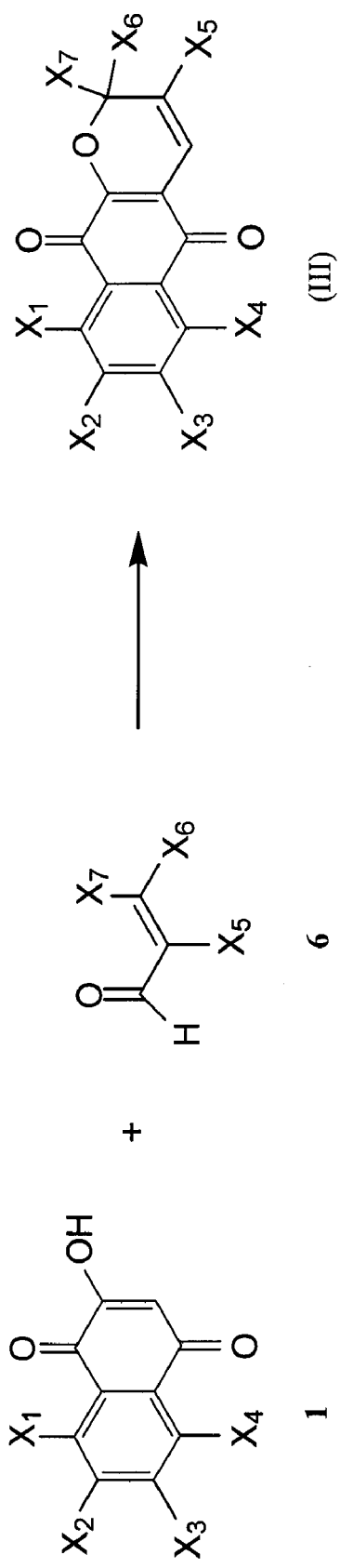
FIG. 3 provides a scheme for the synthesis of the pyran ring of naphtha[2,3-b]pyranoquinones A.
Figure 4:
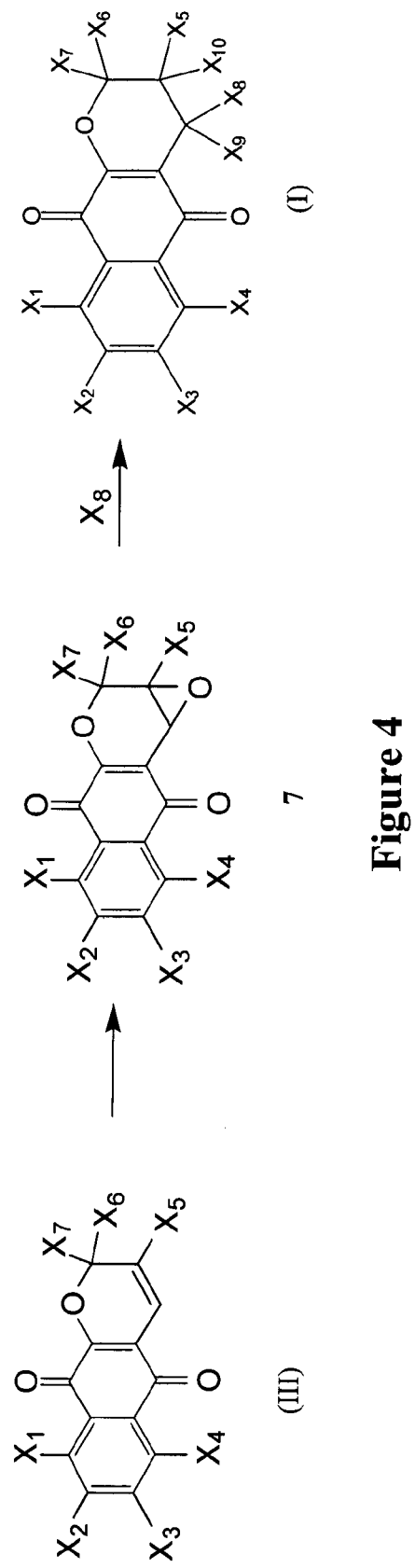
FIG. 4 provides a scheme for the further derivitization of a pyran ring.

Compounds of formula I may by synthesized by the following three stages: 1) synthesizing substituted 2-hydroxy-1,4-naphthoquinones 1 (FIG. 1); 2) generating a pyran ring (FIG. 3); and 3) derivatizing the pyran ring (FIG. 4).

Figure 2:
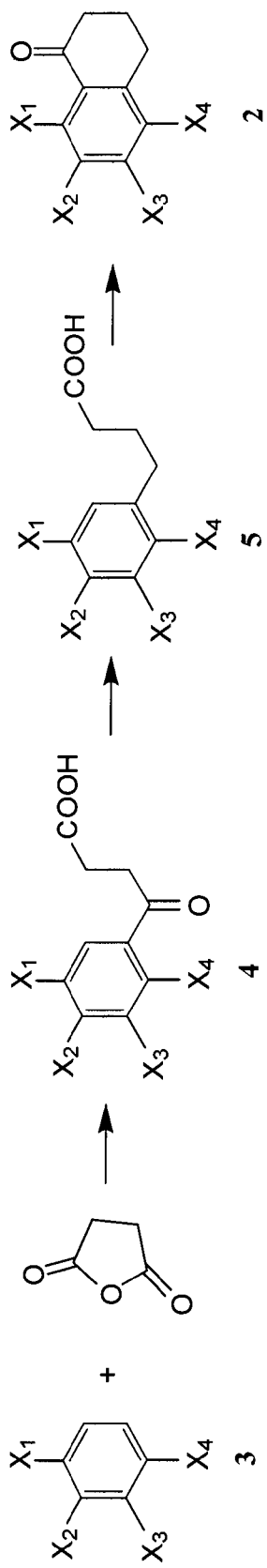
FIG. 2 provides a scheme for the synthesis of 1-tetralone derivatives.

Substituted 2-hydroxy-1,4-naphthoquinones 1 may be synthesized from 1-tetralone derivatives 2 via the oxidation protocol described by Coombe, R. G. (Aust. J. Chem. (1974) 27:1327-30; FIG. 1). The 1-tetralone derivatives 2 may be synthesized as shown in FIG. 2 using procedures described in Coombe, R. G. (Aust. J. Chem. (1974) 27:1327-30; El-Ferlay et al. (Can. J. Chem. (1985) 63:2232-2236; Andrew et al. (Tetrahedron (1985) 41:2933-2938; Srinivas et al. (Organ. Proc. Res. Dev. (2004) 8:291-292; and Ferraz et al. (Tetrahedron (2003) 59:5817-5821.

The pyran ring of the compounds of formula I may be synthesized as depicted in FIG. 3, which shows the generation of formula III. Generally, a solution of 2-hydroxy-1,4-naphthoquinone, 3-methyl-2-butenal (or related α,β-unsaturated aldehyde, 1.25 equiv.), β-alanine (0.15 equiv.), and acetic acid (0.375 mL/1 mmol napthoquinone) in benzene (15 mL/mmol naphthoquinone) is heated to reflux for 18 hours. The reaction mixture is then concentrated in vacuo. Flash chromatography (5% EtOAc: hexanes) affords the pyranon-aphthoquinone product.

Three exemplary methods for the synthesis of three pyran rings are provided below.

First, 2-hydroxy-1,4-naphthoquinone was used with 3-methyl-2-butenal as the aldehyde to yield compound 8. The product spectra were identical to previously reported information for the same compound (see Lee et al. (Synthesis (2005) 18:3026-3034).

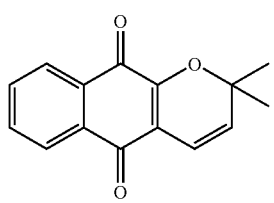

8

Second, 2-hydroxy-1,4-naphthoquinone was used with (E)-methyl-4-oxobut-2-enoate as the aldehyde to provide compound 9. (E)-Methyl 4-oxobut-2-enoate was synthesized as described by Wolff et al. (Tetrahedron Lett. (2002) 43:2555-2559).

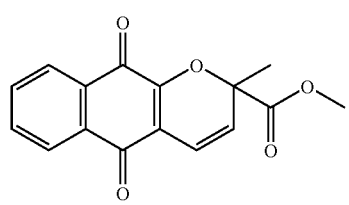

9

Third, 2,5-Dihydroxy-1,4-naphthoquinone was used with 3-methyl-2-butenal as the aldehyde to afford compound 10. The synthesis followed the procedure described by Oliveria et al. (Tetrahedron Lett. (1988) 29:155-158).

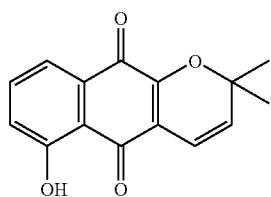

10

Derivatization (i.e., adding substituents) of the pyran ring may be performed by derivatization techniques described in the literature. For example, compounds II-14 were synthesized following the procedure described by Lee et al. (Synthesis (2005) 18:3026-3034).

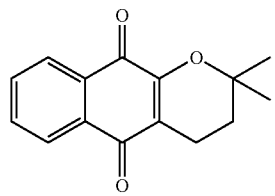

11

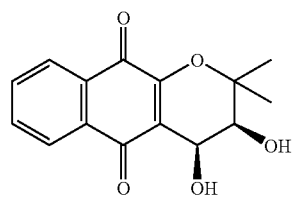

12

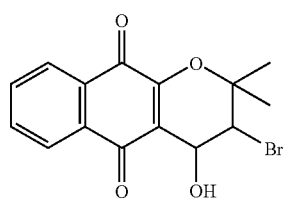

13

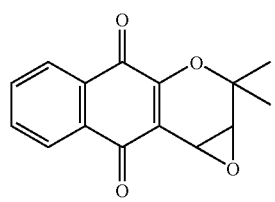

14

Further derivatization of the pyran ring may be performed in accordance with the general procedure shown in FIG. 4 and described in Lee et al. (Synthesis (2005) 18:3026-3034). Specifically, compounds 15-22 and related structures were synthesized by treating compound 14 with various nucleophiles ($X_8$, e.g., benzyl amine, allyl amine, butyl amine, and methanol) and Lewis acid reagents.

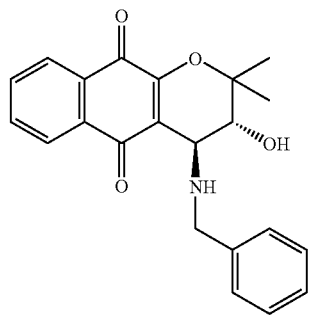

15

-continued

16
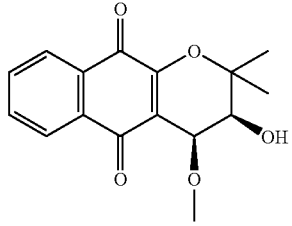

17
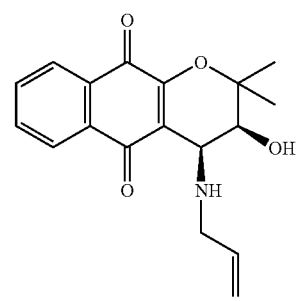

18
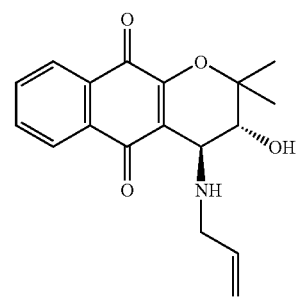

19
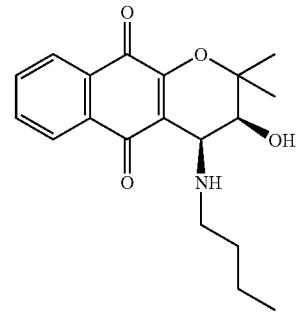

20
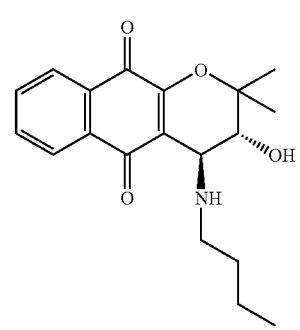

-continued

21
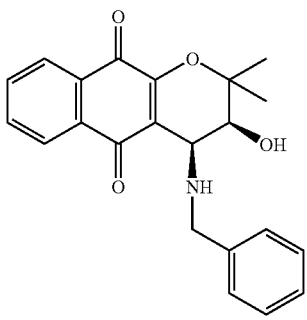

22
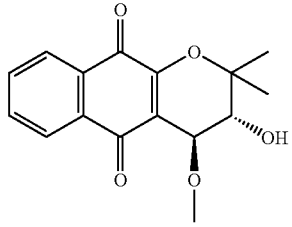

Example 2

Synthesis of Compounds of Formula II

Figure 5:
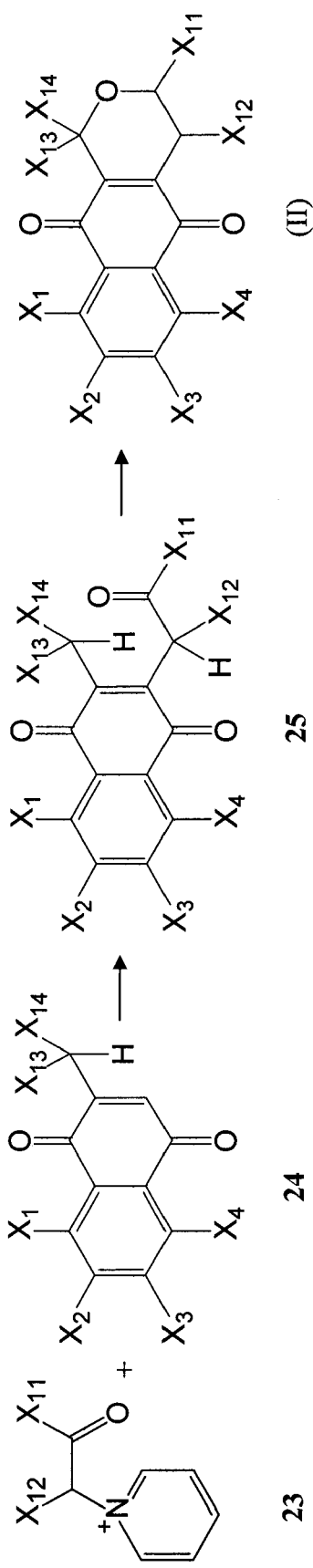
FIG. 5 provides a scheme for the synthesis of naptho[2,3-c]pyranoquinones.

Compounds of formula II may be synthesized in a single pot by reacting 1,4-naphthoquinones with N-acetyl-pyridinium salts 23 as depicted in FIG. 5 and described, in part, by Aldersley et al. (J. Chem. Soc. Perkin Trans. 1 (1990) 8:2163-2174) An exemplary compound obtained by this procedure is compound 26.

26
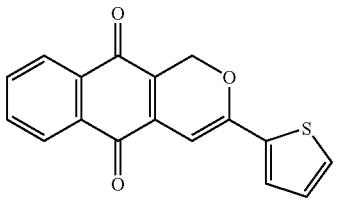

Example 3

IDO Inhibitory Activity

Compounds of the instant invention were analyzed for inhibition of human IDO. The assay was conducted according to a literature protocol, with ascorbic acid and methylene blue serving the role of reductant (Littlejohn et al. (2000) Protein Expression and Purification, 19:22-29; Sono et al. (1989) J. Biol. Chem., 264:1616-1622). Catalase was added to prevent IDO decomposition from peroxide side products (Ohnishi et al. (1977) J. Biol. Chem., 252:4643-4647). The enzyme assay monitored for formation of N-formylkynurenine by hydrolyzing the formyl group and spectrophotometrically analyzing for the conjugated imine generated from kynurenine and 4-(dimethylamino) benzaldehyde.

Specifically, the inhibition assays were performed in a 96-well microtiter plate as previously described with a small modification (Littlejohn et al. (2000) Prot. Expr. Purif., 19:22-29). Briefly, the reaction mixture contained 50 mM potassium phosphate buffer (pH 6.5), 40 mM ascorbic acid, 400 μg/ml catalase, 20 μM methylene blue and purified recombinant IDO(1) optimized based on its activity. The reaction mixture was added to the substrate, L-tryptophan (L-Trp), and the inhibitor. The L-Trp was serially diluted from 200 to 25 μM and the inhibitors were tested at two concentrations, 200 and 400 μM. The reaction was carried out at 37° C. for 60 minutes and stopped by adding 30% (w/v) trichloroacetic acid. The plate was heated at 65° C. for 15 minutes to convert formylkynurenine to kynurenine and then was spun at 6000 g for 5 minutes. Finally 100 μl supernatant from each well was transferred to a new 96 well plate and mixed with 2% (w/v) p-dimethylamino-benzaldehyde in acetic acid. The yellow color generated from the reaction with kynurenine was measured at 490 nm using a Synergy HT microtiter plate reader (Bio-Tek, Winooski, Vt.). The data was analyzed using Graph Pad Prism 4 software (Graph Pad Software Inc., San Diego, Calif.). The results of the IDO inhibition assay are presented in Table 1.

TABLE 1

| Compound Structure | Compound Name (Compound Number) | IC50 (μM) |
|---|---|---|
| 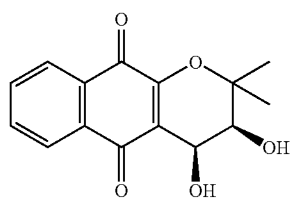 [SMILES: CC1(C)OC2=C(C(=O)c3ccccc3C2=O)[C@H](O)[C@@H]1O] | (3S,4S)-3,4-dihydroxy-2,2-dimethyl-3,4-dihydro-2H benzo[g]chromene-5,10-dione (+ enantiomer) (12) | 1.50 |
| 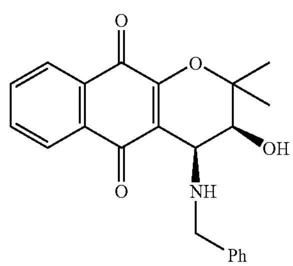 [SMILES: CC1(C)OC2=C(C(=O)c3ccccc3C2=O)[C@H](NCc2ccccc2)[C@@H]1O] | (3S,4S)-4-(benzylamino)-3-hydroxy-2,2-dimethyl-3,4-dihydro-2H-benzo[g]chromene-5,10-dione (+ enantiomer) (16) | 0.125 |
| 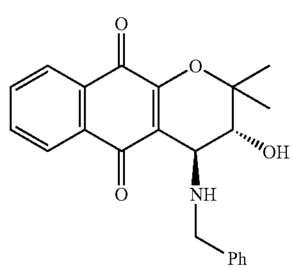 [SMILES: CC1(C)OC2=C(C(=O)c3ccccc3C2=O)[C@H](NCc2ccccc2)[C@H]1O] | (3R,4S)-4-(benzylamino)-3-hydroxy-2,2-dimethyl-3,4-dihydro-2H-benzo[g]chromene-5,10-dione (+ enantiomer) (15) | 0.252 |
| 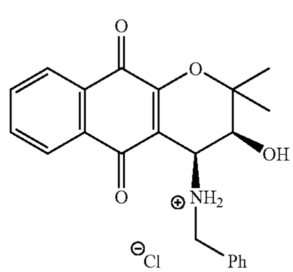 [SMILES: CC1(C)OC2=C(C(=O)c3ccccc3C2=O)[C@H]([NH2+]Cc2ccccc2)[C@@H]1O ; [Cl-]] | (3S,4S)-N-benzyl-3-hydroxy-2,2-dimethyl-5,10-dioxo-3,4,5,10-tetrahydro-2H-benzo[g]chromen-4-aminium chloride (26) | 0.286 |
| 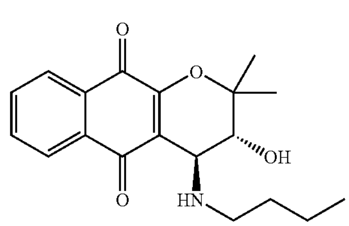 [SMILES: CCCCN[C@H]1C2=C(OC(C)(C)[C@@H]1O)C(=O)c1ccccc1C2=O] | 4-(butylamino)-3-hydroxy-2,2-dimethyl-3,4-dihydro-2H-benzo[g]chromene-5,10-dione (20) | 0.070 |

TABLE 1-continued

| Compound Structure | Compound Name (Compound Number) | IC50 (μM) |
|---|---|---|
| 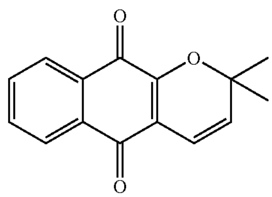 [SMILES: CC1(C)C=CC2=C(O1)C(=O)c1ccccc1C2=O] | 2,2-dimethyl-2H-benzo[g]chromene-5,10-dione (8) | 0.155 |
| 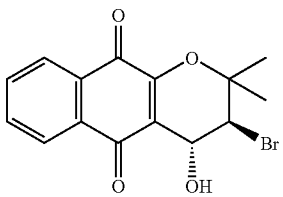 [SMILES: CC1(C)OC2=C(C(=O)c3ccccc3C2=O)[C@@H](O)[C@@H]1Br] | trans-3-bromo-4-hydroxy-2,2-dimethyl-4,4a-dihydro-2H-benzo[g]chromene-5,10(3H,10aH)-dione (27) | 0.29 |
| 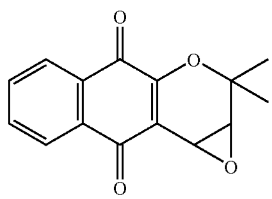 [SMILES: CC1(C)OC2=C(C(=O)c3ccccc3C2=O)C2OC21] | 2,2-dimethyl-9a,9b-dihydro-1aH-benzo[g]oxireno[2,3-c]chromene-4,9(2H,3aH)-dione (14) | 3.3 |
| 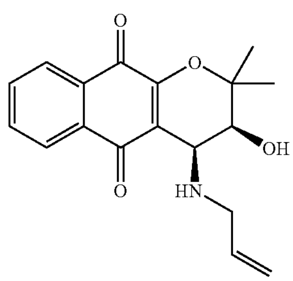 [SMILES: C=CCN[C@H]1C2=C(OC(C)(C)[C@H]1O)C(=O)c1ccccc1C2=O] | 4-(allylamino)-3-hydroxy-2,2-dimethyl-3,4-dihydro-2H-benzo[g]chromene-5,10-dione (17) | 0.183 |
| 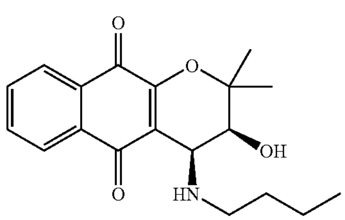 [SMILES: CCCCN[C@H]1C2=C(OC(C)(C)[C@H]1O)C(=O)c1ccccc1C2=O] | 4-(butylamino)-3-hydroxy-2,2-dimethyl-3,4-dihydro-2H-benzo[g]chromene-5,10-dione (19) | 0.160 |
| 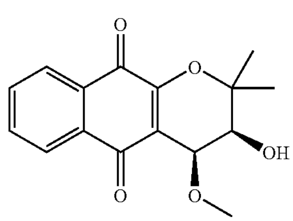 [SMILES: CO[C@H]1C2=C(OC(C)(C)[C@H]1O)C(=O)c1ccccc1C2=O] | 3-hydroxy-4-methoxy-2,2-dimethyl-3,4-dihydro-2H-benzo[g]chromene-5,10-dione (21) | 0.976 |
| 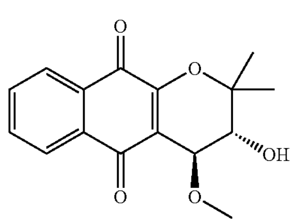 [SMILES: CO[C@H]1C2=C(OC(C)(C)[C@@H]1O)C(=O)c1ccccc1C2=O] | 3-hydroxy-4-methoxy-2,2-dimethyl-3,4-dihydro-2H-benzo[g]chromene-5,10-dione (22) | 3.96 |

TABLE 1-continued

| Compound Structure | Compound Name (Compound Number) | IC50 (μM) |
|---|---|---|
| 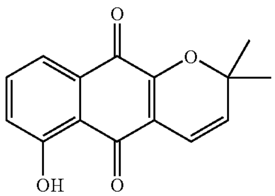 [SMILES: CC1(C)C=CC2=C(O1)C(=O)c1cccc(O)c1C2=O] | 6-hydroxy-2,2-dimethyl-2H-benzo[g]chromene-5,10-dione (28) | 0.058 |
| 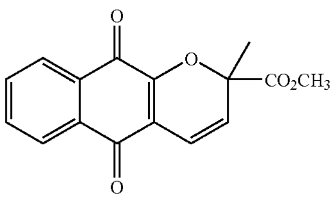 [SMILES: COC(=O)C1(C)C=CC2=C(O1)C(=O)c1ccccc1C2=O] | methyl 2-methyl-5,10-dioxo-5,10-dihydro-2H-benzo[g]chromene-2-carboxylate (29) | 0.161 |

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated compound having indoleamine 2,3 dioxygenase (IDO) inhibitory activity, said compound having the formula of:

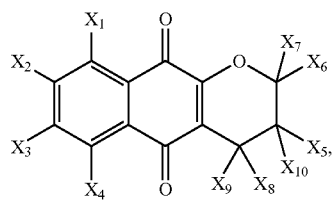

(I)

wherein $X_9$ and $X_{10}$ are H or OH; wherein $X_1$, $X_2$, $X_3$, $X_4$, $X_5$, $X_6$, and $X_7$ are independently selected from the group consisting of halide, H, OH, R, OR, NHR, and SR; wherein R is selected from the group consisting of an alkyl group, cyclic alkyl group, and aryl group; and wherein $X_8$ is NH-alkyl or NH-cyclic alkyl.

2. The compound of claim 1, wherein $X_1$, $X_2$, $X_3$, $X_4$, $X_9$, and $X_{10}$ are H, $X_6$ and $X_7$ are alkyl, $X_5$ is OH, halide, or OR, and $X_8$ is NH-alkyl or NH-cyclic alkyl.

3. The compound of claim 2, wherein $X_1$, $X_2$, $X_3$, $X_4$, $X_9$, and $X_{10}$ are H, $X_6$ and $X_7$ are alkyl, $X_5$ is OH, and $X_8$ is NH-alkyl or NH-cyclic alkyl.

4. The compound of claim 3, wherein $X_8$ is NH-alkyl.

5. The compound of claim 3, wherein $X_6$ and $X_7$ are methyl.

6. A pharmaceutical composition for the treatment of cancer comprising a pharmaceutically acceptable carrier and an effective amount at least one indoleamine 2,3-dioxygenase (IDO) inhibitor, wherein at least one of said IDO inhibitors is the compound of claim 1.

7. The pharmaceutical composition of claim 6, further comprising at least one signal transduction inhibitor (STI).

8. The pharmaceutical composition of claim 6, further comprising at least one chemotherapeutic agent.

9. The pharmaceutical composition of claim 8, wherein said at least one chemotherapeutic agent is selected from the group consisting of paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

10. A compound which is 4-(butylamino)-3-hydroxy-2,2-dimethyl-3,4-dihydro-2H-benzo[g]chromene-5,10-dione.

11. A composition comprising the compound of claim 10 and a pharmaceutically acceptable carrier.

12. An isolated compound having indoleamine 2,3 dioxygenase (IDO) inhibitory activity, said compound having the formula of:

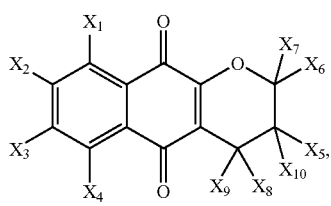

(I)

wherein $X_9$ and $X_{10}$ are H or OH; wherein $X_1$, $X_2$, $X_3$, $X_4$, $X_5$, $X_6$, and $X_7$ are independently selected from the group consisting of halide, H, OH, R, OR, NHR, and SR; wherein $X_8$ is NHR; and wherein R is selected from the group consisting of an alkyl group, cyclic alkyl group, and aryl group, with the proviso that $X_8$ is not NH-phenyl.

13. A composition comprising the compound of claim 12 and a pharmaceutical acceptable carrier.

14. An isolated compound having indoleamine 2,3 dioxygenase (IDO) inhibitory activity, said compound having the formula of:

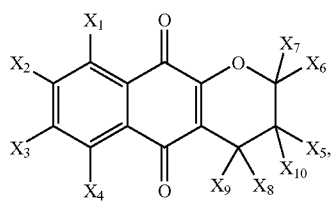

(I)

wherein $X_9$ and $X_{10}$ are H or OH; wherein $X_1$, $X_2$, $X_3$, $X_5$, $X_6$, and $X_7$ are independently selected from the group consisting of halide, H, OH, R, OR, NHR, and SR; wherein R is selected from the group consisting of an alkyl group, cyclic alkyl group, and aryl group; and wherein $X_8$ is selected from the group consisting of NH-alkyl, NH-cyclic alkyl, NH-benzyl, NH-allyl, NH-naphthyl, NH-indolyl, and NH-pyridyl.

15. A composition comprising the compound of claim 14 and a pharmaceutical acceptable carrier.

* * * * *

UNITED STATES PATENT AND TRADEMARK OFFICE
CERTIFICATE OF CORRECTION

PATENT NO.       : 8,389,568 B2
APPLICATION NO.  : 12/528466
DATED            : March 5, 2013
INVENTOR(S)      : Prendergast et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 602 days.

Signed and Sealed this
First Day of September, 2015

Michelle K. Lee
*Director of the United States Patent and Trademark Office*